(12) United States Patent
Zhang et al.

(10) Patent No.: US 9,259,453 B2
(45) Date of Patent: Feb. 16, 2016

(54) **USE OF *SALMONELLA* FLAGELLIN DERIVATIVE IN PREPARATION OF DRUG FOR PREVENTING AND TREATING INFLAMMATORY BOWEL DISEASES**

(75) Inventors: Chenggang Zhang, Beijing (CN); Junhuai Li, Jiangsu Province (CN); Yang Xu, Beijing (CN); Yonghong Wu, Beijing (CN); Weiguang Li, Beijing (CN); Yanchun Zhang, Beijing (CN); Yan Gao, Beijing (CN); Zhihui Li, Beijing (CN)

(73) Assignees: Suzhou Sciscape Biomedicine Science & Technology Co. Ltd., Jiangsu Province (CN); Institute of Radiation Medicine, Academy of Military Medical Sciences, People's Liberation Army of China, Beijing (CN)

( * ) Notice: Subject to any disclaimer, the term of this patent is extended or adjusted under 35 U.S.C. 154(b) by 0 days.

(21) Appl. No.: 14/131,050

(22) PCT Filed: Jan. 19, 2012

(86) PCT No.: PCT/CN2012/000097
§ 371 (c)(1),
(2), (4) Date: Feb. 28, 2014

(87) PCT Pub. No.: WO2013/004069
PCT Pub. Date: Jan. 10, 2013

(65) Prior Publication Data
US 2014/0248348 A1 Sep. 4, 2014

(30) Foreign Application Priority Data
Jul. 5, 2011 (CN) .......................... 2011 1 0186065

(51) Int. Cl.
*C07K 14/255* (2006.01)
*A61K 38/16* (2006.01)
*A61K 9/28* (2006.01)

(52) U.S. Cl.
CPC .............. *A61K 38/164* (2013.01); *A61K 9/2806* (2013.01); *C07K 14/255* (2013.01)

(58) Field of Classification Search
CPC .............. A61K 38/164; A61K 39/0208; C07K 2319/00; C07K 14/255
See application file for complete search history.

(56) References Cited

FOREIGN PATENT DOCUMENTS

| CN | 101411872 A | 4/2009 |
|---|---|---|
| CN | 102046198 A | 5/2011 |
| EP | 1841785 A2 | 10/2007 |
| WO | 2006/069198 A1 | 6/2006 |
| WO | 2006/078657 | 7/2006 |

OTHER PUBLICATIONS

Burdelya, L.G. et al., "An Agonist of Toll-Like Receptor 5 Has Radioprotective Activity in Mouse and Primate Models" *Science* (2008) pp. 226-230, vol. 320, No. 5873.
Abreu, M.T. et al., "Decreased expression of Toll-like receptor-4 and MD-2 correlates with intestinal epithelial cell protection against dysregulated proinflammatory gene expression in response to bacterial lipopolysaccharide" *J Immunol* (Aug. 1, 2001) pp. 1609-1616, vol. 167, No. 3.
International Search Report dated Apr. 26, 2012 issued in International Application No. PCT/CN2012/000097.
Supplementary European Search Report issued in EP Application No. 12 80 7820, mailed Feb. 16, 2015.
Cairo, E. "Toll-like Receptors in Inflammatory Bowel Diseases: A Decade Later" Inflamm Bowel Dis 16(9):1583-1597 (2010).
Vijay-Kumar, M. et al. "Role of Flagellin in Chron's Disease: Emblematic of the Progress and Enigmas in Understanding Inflammatory Bowel Disease" 15(5)190-795 (2009).
Rhee, S. H. et al. "Pathophysiological role of Toll-like receptor 5 engagement by bacterial flagellin in colonic inflammation" PNAS 102(38):13610-13615 (2005).

*Primary Examiner* — Karen Cochrane Carlson
(74) *Attorney, Agent, or Firm* — Scully, Scott, Murphy & Presser, P.C.

(57) ABSTRACT

The application of flagellin derivative CZLC31 from *Salmonella* in preparation of medicines for preventing and treating inflammatory bowel disease (IBD) is introduced in this invention. The CZLC331 protein has a good preventive and therapeutic effect for IBD, such as ulcerative colitis (UC) and Crohn's disease (CD) in this invention. Therefore, this protein can be prepared into the drug for prevention and treatment of IBD. It has been found that the bad efficacy, slow onset, long course of treatment, side effects can be significantly avoided for existing clinical IBD drugs, it can reduce the patient's pain during the treatment in this invention. The rehabilitation and quality of life of the patients have been largely improved. The drug will play an important role in the prevention and treatment of IBD in this invention, and has broad application prospects.

16 Claims, 7 Drawing Sheets

A:0.2mg/kg、B:0.4mg/kg、C: 0.8mg/kg、D:1.6mg/kg

USE OF *SALMONELLA* FLAGELLIN DERIVATIVE IN PREPARATION OF DRUG FOR PREVENTING AND TREATING INFLAMMATORY BOWEL DISEASES

CROSS REFERENCE TO RELATED APPLICATIONS

This application is the national phase of International Application No. PCT/CN2012/000097 filed Jan. 19, 2012, the entire contents of which are incorporated herein by reference.

INCORPORATION BY REFERENCE OF SEQUENCE LISTING

The Sequence Listing in an ASCII text file, named 30742 SEQ revised ST25.txt of 13 KB, created on Sep. 23, 2015, and submitted to the United States Patent and Trademark Office via EFS-Web, is incorporated herein by reference.

TECHNICAL FIELD

This invention belongs to the new application of recombinant protein in medicine and drug, in particular to the new application of a flagellin derivative from *Salmonella*, named CZLC331, in the prevention and treatment of inflammatory bowel disease (IBD).

BACKGROUND OF THE INVENTION

Ulcerative colitis (UC), also known as idiopathic ulcerative colitis or chronic nonspecific ulcerative colitis, is a disease of large intestine with infiltration of the mucosa and idiopathic chronic non-specific inflammation. The main clinical symptoms are abdominal pain, diarrhea, mucus and bloody stools, and associated with optic neuritis, neuritis, and osteoporosis. It has been characterized as a hardy disease by the World Health Organization (WHO) because treatment of the disease is difficult and time-consuming and the disease relapses easily. Although currently there are a variety of drugs for curing IBD, such as amino salicylic acid, glucocorticoids and immunosuppressive agents, but they have many shortcomings, such as poor efficacy (especially to severe UC), slow onset, long course, and large side effects. Therefore, the drug with an effective, rapid onset, short course, high safety, little side effects, convenient for IBD (especially chronic nonspecific ulcer colitis) is urgently needed.

It has been shown that CBLB502, one of the flagellin derivatives from *Salmonella*, has a protective effect on the hematopoietic system, and can extend the survival time of mice to the high-dose radiation injury and improve the survival rates of low-dose irradiated mice (Lyudmila G. Burdelya, et al,. An Agonist of Toll-Like Receptor 5 Has Radioprotective Activity in Mouse and Primate Models. Science 2008; 320 (5873): 226-230). The study found that the flagellin protein derivatives from *Salmonella* and other derivants containing the N-and C-terminal conserved domain have the radial protection, they can effectively improve the number of hematopoietic stem cells in the bone marrow of mice and effective preventing the death of mice caused by lethally irradiation. Its mechanism may be the anti-apoptotic role through NF-κB signal pathway. It means that this protein can be applied to development of anti-radiation drugs. There is no report on *Salmonella flagellin* derivatives except for the anti-radiation drug.

SUMMARY OF THE INVENTION

The object of this invention is to provide a flagellin derivative of *Salmonella*, named CZLC331, in the prevention and treatment for IBD.

The CZLC331 has a good preventive and therapeutic effect for IBD such as ulcerative colitis (UC) and Crohn's disease (CD) in this invention. Therefore, this protein can be developed as a candidate drug for the prevention and treatment of IBD.

The CZLC331 protein of this invention having the amino acid sequence shown in SEQ ID NO: 3 includes a Tat protein transduction peptide and N-terminal amino acid residues 1-176 and 402-505 of *Salmonella* flagellin. The fusion protein may be connected by a flexible linker peptide.

The CZLC331 can be prepared using conventional prokaryotic expression, and the purity is more than 95%. The preparation methods of CZLC331 includes following steps:

1) The gene encoding CZLC296 is synthesized, and the nucleotide sequence is shown in SEQ ID NO: 1 . The CZLC296 protein having the amino acid sequence shown in SEQ ID NO: 4 includes a flexible linker which connects the N terminal 1-176 and the N-terminal 402-505 amino acid residues of the *Salmonella*flagellin protein.

2) The DNA sequence coding for the *Salmonella flagellin* derivative CZLC296 was subcloned into a prokaryotic expression vector which included the coding sequence of the Tat transduction peptide. The DNA sequence coding for the Tat protein transduction peptide could also be subcloned into a prokaryotic expression vector carrying the DNA sequence for CZLC296. The resulting flagellin derivative was named as CZLC331, and the nucleotide sequence is shown in SEQ ID NO: 2.

3) The recombinant expression vector pET28b-Tat-CZLC331 was transformed into the host bacteria.

4) The coding sequence of Tat transduction peptide and the host bacteria which carrying the prokaryotic expression vector of CZLC296 were induced and expressed.

5) The recombinant protein was isolated and purified, and got the protein of CZLC331.

The prokaryotic expression vectors of carrying coding sequence of Tat transduction peptide is one prokaryotic expression vectors of *E. coli* in the preparation of CZLC331, pET-22b, pET-28, or pET-15, the best is pET28b-Tat. The prokaryotic expression vector of CZLC331 is pET28b-Tat-CZLC331 which carries the coding sequence of Tat transduction peptide.

The host bacteria is *E. coli* BL21(DE3), *E. coli* ER2566 (DE3), *E. coli* BL21(DE3) plysS, *E. coli* JM109, *E. coli* HB101 or *E. coli* Top10 in step 3). The best host bacterium is *E. coli* BL21 (DE3).

The drug containing CZLC331 protein can be prepared into injection, oral, enema, capsules, enteric-coated tablets, powders or tablets, and the better is injection, enema, or enteric-coated tablets in this invention.

The above-described drugs can be administered in various dosage forms according with the conventional method in the pharmaceutical field.

The active pharmaceutical ingredient of CZLC331 can be 1-35% in capsules, enteric-coated tablets, powders, granules.

The concentration of CZLC331 can be 2-64 g/L in injection, oral and enema liquid dosage forms.

When necessary, one or more pharmaceutically acceptable excipients can also be added to the above drugs, including absorption accelerators, surfactants, lubricants, stabilizers, diluents, bonding agents, wetting agents, disintegrants, diluents, adsorption carrier, and excipient. If necessary, colorings, sweeteners and flavoring agent may also be added.

Specifically, the drug is a protein injection, and the component of this drug is CZLC331 what ratio of weight/volume is 5% (5 g/100 ml), sodium chloride (0.85%, 0 85 g/100 ml) and water for injection.

Alternatively, the drug is coated tablets, and the component is CZLC331 100, lactose 60, microcrystalline cellulose 20, sodium carboxymethyl starch 20, $K_{30}$ 10 granulation 20. And then mixed evenly tablet was made by dry particles 2500: talc tableting 50, and spray coated enteric film-coated layer is made in the table side.

The dosage of this drugs is generally 0. 2-6. 4 mg CZLC331 protein/kg body weight, and is administered 1-2 times a day, the course is 5-10 days. The injection can be given by intramuscular injection, intraperitoneal injection or intravenous injection.

It is shown the new application of CZLC331 in IBD in this invention. CZLC331 has the obvious prevention and therapeutic effects for IBD through the simulate experiment of human ulcerative colitis by giving 2,4, 6-trinitrobenzene sulfonic acid (TNBS). The results are 1) model group: the feeding/drinking water of mice significantly reduced, the activities reduced and accompanied by blood in the stool. There are visible congestion, edema, bleeding and ulcers in the colon. And it is visible about the cell structural disorder, disappearance of goblet cells, lymphocytes, and neutrophils infiltration under the microscope. 2) intraperitoneal administration group: the feeding/water intake of mice return to normal, the activities increased significantly and reduce blood in the stool. The visible congestion, edema, bleeding and ulcers in the colon are significantly reduced. And the cell structural disorder, disappearance of goblet cells, lymphocytes, and neutrophils infiltration under the microscope are significantly reduced. The experimental results show that intraperitoneal injection CZLC331 may be effective against colon inflammation on intestinal damage, and has played a protective role in inflammation in mice. Thus, it is possible that CZLC331 protein was made as active drugs for IBD. The drug has the following advantages: 1) significant effect (effective rate is 100%, the cure rate is 70%), while the effective rate of clinical drug sulfasalazineis only about 90%, and the markedly effective rate was only 50%; 2) rapid onset (24 hours after administration to onset), sulfasalazine is about two weeks, and then the symptoms was improved; 3) short course (treatment is usually 5-10 days), sulfasalazine treatment is usually about 6 weeks; 4) safe (non-toxic), and patients who taking sulfasalazine alanine have elevated aminotransferase (ALT) and aspartate aminotransferase (AST), these suggesting that there is liver toxicity; 5) small side effects (no significant side effects), but there are nausea, rash, neutropenia after taking sulfasalazine; 6) medication convenient (intraperitoneal injection once daily), and sulfasalazine is 3-4 g/d, 3-4 times a day orally. In summary, the CZLC331 can solve the poor efficacy, slow onset, long course of treatment, side effects of existing treatment drugs for IBD, and it can significantly reduce the pain of patient, promote physical rehabilitation, and improve the patient's quality of life. It will be play an important role in the prevention and treatment of IBD in this invention, and it has broad application prospects.

DETAIL DESCRIPTION OF THE EMBODIMENTS

Figure 1:
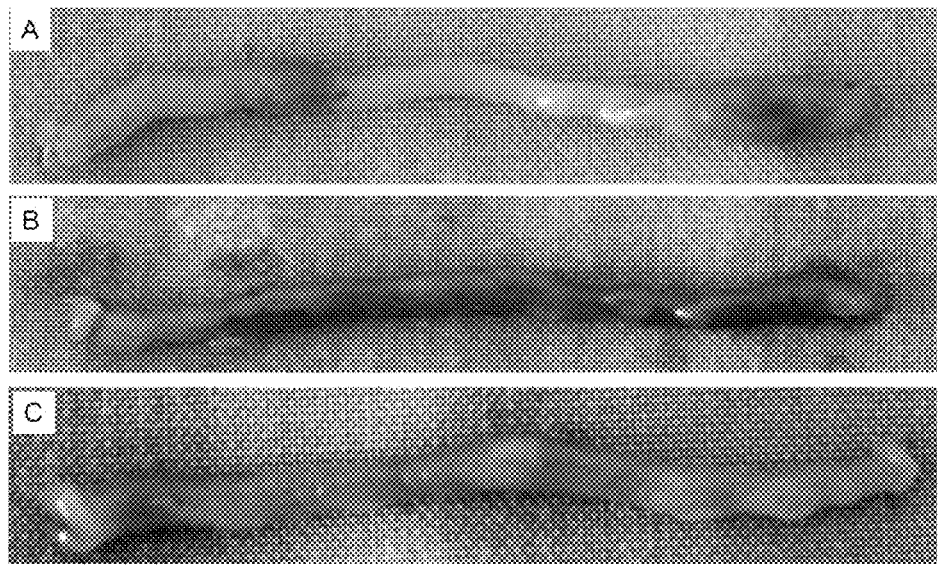
FIG. 1 The colon appearance of mice with UC after 0.5 h treating with 0.2 mg/kg CZLC331 protein in trinitrobenzene sulfonic acid (TNBS) modeling.

In order to study the new features of *Salmonella flagellin* and to develop as a new drug, it was found that CZLC331 may be cut TLRs expression in IBD, such as UC and Crohn's disease, and has a good preventive and therapeutic effect.

It was reported that intestinal epithelial cells can maintain intestinal immune tolerance by down-regulating the expression of TLR4 (Abreu MT, Vora P, Faure E, Thomas L S, Arnold E T, Ardit i M. Decreased expression of Tol 11 ike receptor-4 and MD-2 correlates with intest inal epithel ial cel 1 protect ion against dysregulated proinflammatory gene expression in response to bacterial lipopolysaccharide. *J Immunol*, 2001 Aug 1;167(3):1609-16). It was unexpectedly found that *Salmonella flagellin* has a role in the prevention and treatment of UC, and the further evidence suggested that this effect is achieved by down-regulating the expression of TLR in colon.

Toll-like receptor (TLR) family is a receptor protein which has a homology with the Drosophila Toll protein, it belongs to the pattern recognition receptors. The main function is identifying the conservative structure of pathogenic microorganisms, improve immune system through a variety of signal transduction ways. The TLR family plays a key role in the anti-infective immunity and innate immunity, and it is also an important to acquired immune regulatory factors. The activation signal is deliveried to the intracellular after TLR identifying pathogens, and activate NF-κB transcription factor. TL-1, IL-6, IL-8 are induced, upregulation of IL-12, TNF. IL-12 is a key regulator for inducting T and B lymphocytes cells in the cell-mediated immune response. It can be used as biological adjuvants specific T cell responses against pathogens. Therefore, it can be said TLR family is the early signal for IL-12 and Th1 cells involved in the immune response. When the balance between TLRs and the normal flora is broken, it will cause pathological intestinal inflammation. In particular, *Salmonella flagellin* has the effect for down-regulating the expression of TLR family in colon tissue, and it may be the important mechanism for its role in the treatment of UC.

The coding sequences of amino acids 1-176 and amino acids 402-505, respectively, of *Salmonella* flagellin were synthesized, and a protein of the total length of 331 amino acids is prepared by prokaryotic expression, and named as CZLC331 (SEQ ID NO: 3). It has been proved that it has a good prevention and treatment for IBD, such as UC and Crohn's disease. It will provide important reference for the prevention and treatment of IBD.

The detailed embodiments and specific procedure are given as follows, but the scope of protection of this invention is not limited to the following embodiments. The methods used in this invention are conventional methods.

Example 1

The Prepared of *Salmonella flagellin* CZLC331

1. The construction of prokaryotic expression vector pET28b-Tat-CZLC331 for expressing CZLC331

1) The coding gene of CZLC296 was synthesized, and the nucleotide sequence as shown in SEQ ID NO: 1. The length of nucleotide sequence is 891bp, it was synthesized by Beijing Bo Mai De Science and Technology Development Co., Ltd. The gene was test using 2% agarose gel electrophoresis, and the result showed that the target gene, 891bp, was conformed to the expected results.

2) The construction of recombinant expression vector pET28b-Tat-CZLC331 a) The coding gene of CZLC296 protein was amplified by PCR.

The coding gene of CZLC331 of 891 bp was amplified using conventional PCR. The reaction system is 50 μ, plasmid template 0.5 μ, what is the cloning vector pGH-CZLC296 carrying CZLC331 coding gene, and the method is CZLC296 coding gene inserted into the SmaI restriction sites of the cloning vector pGH. 10×dNTP 5 μ, 10×Ex Taq buffer 5 μ, the upstream and downstream primers 0.5 μ, and the upstream primer sequence is 5'-CGCGGGATCCATGGCTCAAGT-TATCA-3' (SEQ ID NO: 5), the reverse primer sequence is 5'-CCGCTCGAGTCTCAACAAAGACAAGTT-3' (SEQ ID NO: 6). Ex Taq enzyme 0.25 μl, ddH$_2$O 38.25 μl. The reaction condition of PCR is 95° C. 4 min, 95° C. 45 sec, 56° C. 30 sec, 72° C. 45 sec, total 30 cycles, and then 72° C. 7 min. The PCR product was subjected to 1% agarose gel electrophoresis after completing reaction, and the results show that the amplified DNA of 891bp is consistent with the expected results, and then the target fragment was recovered and purified.

b) The digestion of the target gene CZLC296 and pET28b-TAT vector using restriction endonuclease.

CZLC296 and pET28b-TAT vector were digested using restriction endonuclease BamH I and Xho I. The construction of pET28b-TAT vector is synthesizing the TAT sequence for having the upstream of NcoI and the downstream of NdeI, then digested the TAT sequence and pET28b using restriction endonuclease. The recovered fragment was recycled by T$_4$ DNA ligase and restriction digestion. The sequence was confirmed by Invitrogen Co., Ltd. And then the digested production was transformed into competent cells *E. coli* DH5a using T$_4$ DNA ligase at 16° C.

c) Identification

The culture grown clone was confirmed by digestion of restriction enzyme and sequencing.

The sequencing results show that the obtained sequence and the insertion position were correct, and the recombinant expression vector included the coding sequence of the Tat protein transduction peptide and CZLC296 The vector was named pET28b-Tat-CZLC331. The protein included the Tat protein transduction peptide at the N terminal end of CZLC296 and was named CZLC331. The nucleotide sequence encoding the protein is shown in SEQ ID NO: 2.

2. Transformation and Bacterial Recovery

The prokaryotic expression vector pET28b-Tat-CZLC331 what was constructed correctly was transformed into *E. coli* BL21 (DE3), and then coating to the LB plate what contain the Kana$^+$100 μg/ml. Then the clone was inoculated into 5 mL LB containing Kana$^+$100 μg/mL, the bacteria was shake at 220 rpm for 16 h to be fully recovered bacteria.

3. The inducible Expression of Prokaryotic Expression Vector pET28b-Tat-CZLC331.

The bacteria was recovered, and it was diluted to OD$_{600}$=0.8. Then the bacteria (5 ml) were inoculated into 150 ml LB containing Kana$^+$ (final concentration is 100 μg/ml). The bacteria were shaking at 37° C. approximately 4-5 hours at 220 rpm. The inducing agent IPTG (final concentration 1 mM) was added rapidly to the bacteria when the OD$_{600}$ is 0.6-1.0, and it was induced and expressed at 30° C., 220rpm by 8hours.

4. The Preparation of CZLC331 Protein

The induced and expressed bacteria were collected at 12000 rpm for 10 minutes at 4° C. The bacteria were broke by ultrasound using 20 mM sodium phosphate buffer, and was prepared a CZLC331 protein, and then CZLC331 protein was to be separated and purified.

5. The Separation and Purification of CZLC331 Protein.

The unpurified CZLC331 was directly loaded onto the HisTrap HP 5 ml column (purchased from GE Corporation), and then the peak baseline was washed using 4-5 column volumes of the above buffer. Finally, the protein was washed using elution buffer (20 mM Na$_3$PO$_4$+0.5M NaCl+0.5M imidazole, pH7.4), and then CZLC331 was obtained, which purity is more than 95%.

Example 2

The Effect of CZLC331 for Treatment of IBD

Experimental Animal: Male BALB/c mice (7-8 weeks old, 25±5 g) were obtained from Experimental Animal Center of Academy of Military Medical Sciences (Beijing, China). Mice were provided sterile food and water, and 12 h light/12 h dark cycle. All animal experiments were approved by the Institutional Animal Care and Use Committee at Academy of Military Medical Sciences.

Reagents: 2,4,6-trinitrobenzene sulfonic acid (TNBS, were purchased from Sigma Chemical Co.), CZLC331 (prepared in Example 1), RT PCR kit (ID isFSK100, purchased from Toyobo Biotechnology Co., Ltd.).

Model preparation: Mice (hunger for 36 h) were anesthetized with isoflurane using anesthesia machine. To induce IBD, 150 mg/kg of TNBS (Sigma-Aldrich) in 38% ethanol (to break the intestinal epithelial barrier) was administered by the mouse gavage needle equipped with a 1 ml syringe, what the diameter of silicone tube is 2. 0 mm and the length is about 10 cm, the gavage needle was advanced into the rectum until the tip was 4 cm proximal to the anal verge. The total injection volume was 100 μl.

Experimental animal groups: model group, treatment group and control group (n=8). The control mice received 38% ethanol alone by using the same method described above, and normal feeding two days. The treatment group: BALB/c mice were treated therapeutically with CBLB502 (3.2 mg/kg) at 0.5 h after TNBS administration. At the same time, BALB/c mice were treated therapeutically with CBLB502 (0.2-6.4 mg/kg) from 0.5 h to 8 h after TNBS administration, and normal feeding two days. The mice of model group were normal feeding two days after TNBS administration.

Figure 2:
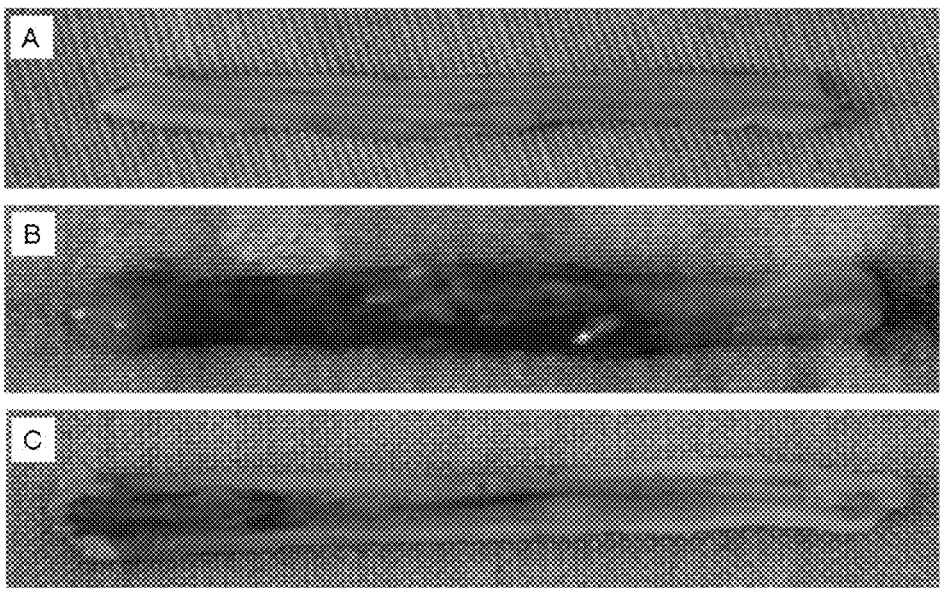
FIG. 2 The colonic mucosa of mice with UC after 0.5 h treating with 0.2 mg/kg CZLC331 protein in trinitrobenzene sulfonic acid (TNBS) modeling.
Figure 4:
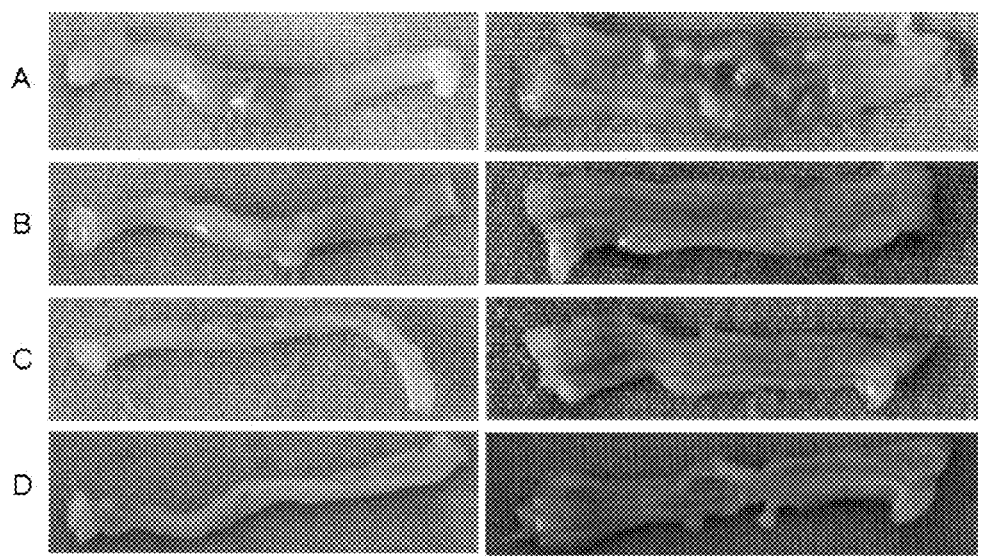
FIG. 4 The colon appearance and colonic mucosa of mice with UC after 0.5 h treating with different concentrations CZLC331 protein in trinitrobenzene sulfonic acid (TNBS) modeling.
Figure 5:
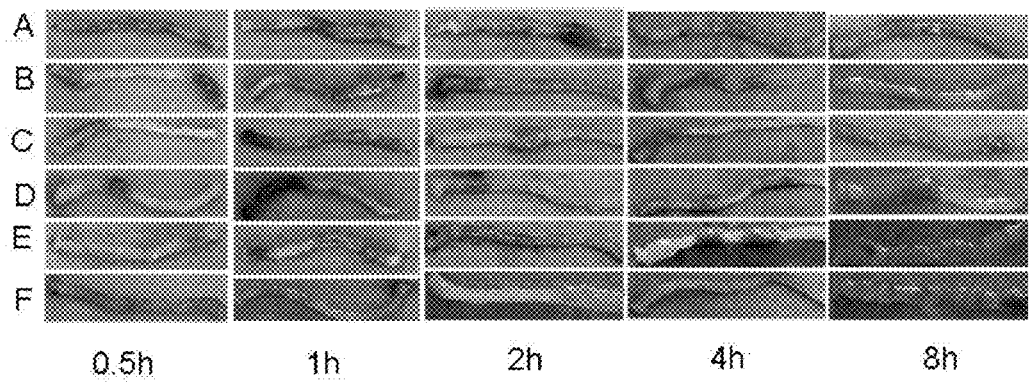
FIG. 5 The colon appearance of mice with UC after different time treating with different concentrations CZLC331 protein in trinitrobenzene sulfonic acid (TNBS) modeling.
Figure 6:
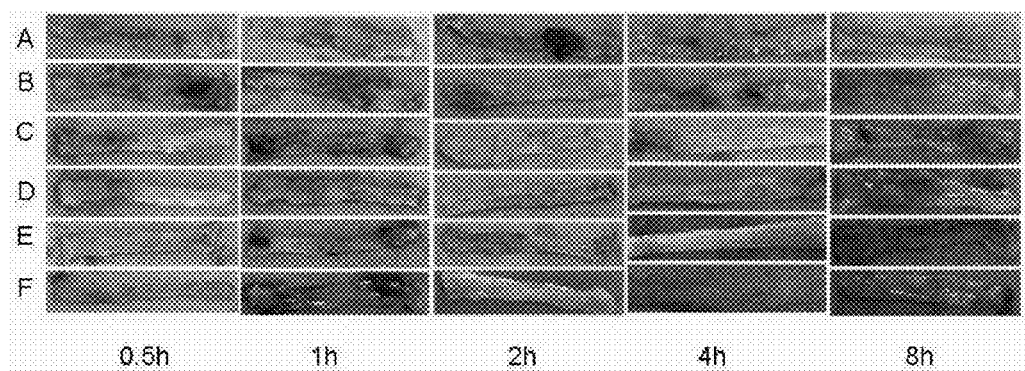
FIG. 6 The colon appearance and colonic mucosa of mice with UC after different time treating with different concentrations CZLC331 protein in trinitrobenzene sulfonic acid (TNBS) modeling.

Mice were monitored for the appearance of diarrhea, changes of body weight, and overall mortality. At the end of the experiment after TNBS administration two days, surviving mice were killed, blood samples were collected by cardiac puncture, and a 7-cm segment of the colon was excised for macroscopic (FIG. 1, FIG. 4 left, and FIG. 5) and microscopic damage evaluation (FIG. 2, FIG. 4 right, and FIG. 6). And the end of the colon after washing using physiological saline was kept at −80° C. frozen for follow-up testing.

Figure 3:
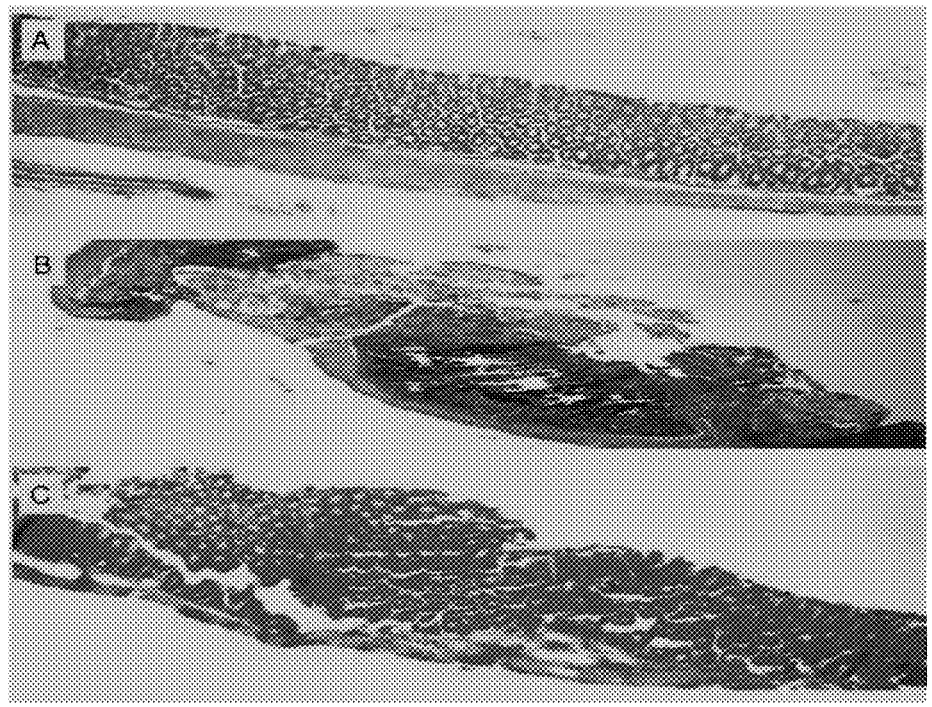
FIG. 3 The colonic mucosa HE staining of mice with UC after 0.5 h treating with 0.2 mg/kg CZLC331 protein in trinitrobenzene sulfonic acid (TNBS) modeling.
Figure 7:
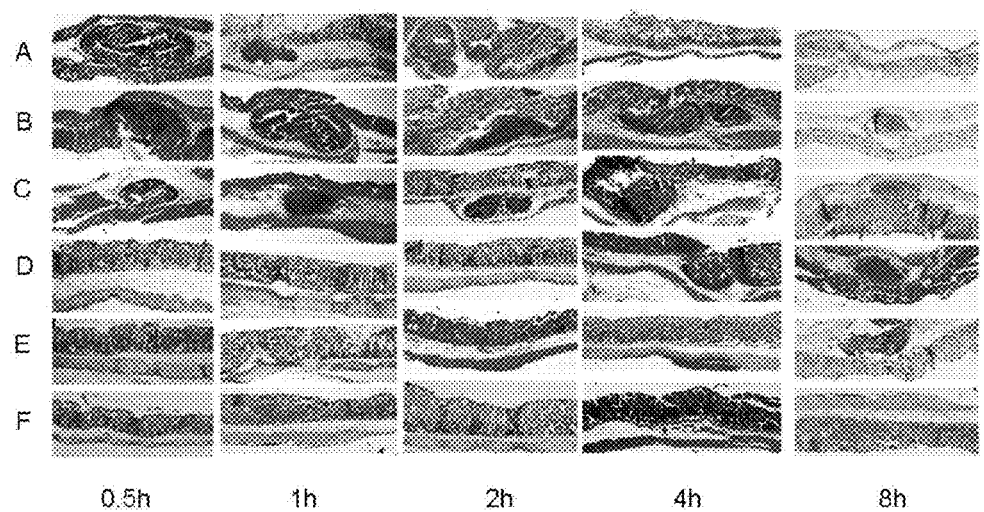
FIG. 7 The colonic mucosa HE staining of mice with UC after different time treating with different concentrations CZLC331 protein in trinitrobenzene sulfonic acid (TNBS) modeling.

1. The results shown that feeding/water and activity were significantly reduced, and there were blood in the stool in model mice. There were significant congestion, edema, hemorrhage, and ulceration in modeling. The colon appearance and colonic mucosa of mice with ulcerative colitis after 0.5 h treating with 0.2 mg/kg CZLC331 protein in TNBS modeling is shown in FIG. 1 and FIG. 2, A is the control group, B is the model group, C is treatment group. The results were structural disorder of cells, disappearance of goblet cells, lymphocytes and neutrophils infiltration under the microscope in model group. The colonic mucosa HE staining of mice with ulcerative colitis after 0.5 h treating with 0.2 mg/kg CZLC331 protein in TNBS modeling is shown in FIG. 3, A is the control group, B is the model group, C is treatment group. The phenomenon of blood in the stool, eat less and move less were reduced. The phenomenon of congestion, edema, hemorrhage began reduce, such as FIG. 1, FIG. 2, FIG. 4 (The colon appearance and colonic mucosa of mice with ulcerative colitis after 0.5 h treating with different concentrations CZLC331 protein in TNBS modeling. A. 0.2 mg/kg CZLC331, B. 0.4 mg/kg CZLC331, C. 0.8 mg/kg CZLC331, D. 1.6 mg/kg CZLC331), FIG. 5 (The colon appearance of mice with ulcerative colitis after different time treating with different concentrations CZLC331 protein in TNBS modeling. A. 0.2 mg/kg CZLC331, B. 0.4 mg/kg CZLC331, C. 0.8 mg/kg CZLC331, D. 1.6 mg/kg CZLC331, E. 3.2 mg/kg CZLC331, F. 6.4 mg/kg CZLC331 ), FIG. 6 (The colon appearance and colonic mucosa of mice with ulcerative colitis after different time treating with different concentrations CZLC331 protein in TNBS modeling. A. 0.2 mg/kg CZLC331, B. 0.4 mg/kg CZLC331, C. 0.8 mg/kg CZLC331, D. 1.6 mg/kg CZLC331, E. 3.2 mg/kg CZLC331, F. 6.4 mg/kg CZLC331). The structures of cells were arranged in neat, a small number of goblet cells and lymphocyte and neutrophil infiltration were disappeared (FIG. 3 and FIG. 7).

The food intake and water intake is normal, and there were no blood in the stool and reduction activities in control mice. The cells arranged in neat rows, no decrease in goblet cells and infiltration of lymphocytes and neutrophils.

2. Histological examination: The colonic samples were fixed in 4% buffered formalin overnight and then transferred to 70% ethanol, embedded in paraffin for sectioning, and then stained with hematoxylin and eosin (H&E) to examine the histological differences.

The colonic mucosa HE staining of mice with ulcerative colitis after 0.5 h treating with 0.2 mg/kg CZLC331 protein in TNBS modeling is shown in FIG. 3. The colonic mucosa HE staining of mice with ulcerative colitis after different time treating with different concentrations CZLC331 protein in TNBS modeling is shown in FIG. 7 (A. 0.2 mg/kg CZLC331, B. 0.4 mg/kg CZLC331, C. 0.8 mg/kg CZLC331, D. 1.6 mg/kg CZLC331, E. 3.2 mg/kg CZLC331, F. 6.4 mg/kg CZLC331). The cells arranged in neat rows, no decrease in goblet cells and infiltration of lymphocytes and neutrophils means that there were well results for treating.

3. The Expression of TLR Family

The colon samples were removed at the indicated times, washed with phosphate-buffered saline (pH 7.2), and cut in small pieces. Total RNA of colon samples what were control group, modeling group and treatment group were extracted by Total RNA kits II (Omega, Japan) according to the manufacturers' instructions, and then reverse-transcribed by the Reverse Transcription System (Sigma, USA). Subsequently, the TLRs and β-actin were amplified by PCR using the following primers (Table 1). The reaction system of PCR was 500, Ex Taq 0.250, 10× buffer 5 µl, dNTP 5 µl, template 2 µl, the upstream and downstream primers 1 µl, ddH$_2$O 35.75 µl. The reaction condition of PCR is 95° C. 5 min, 95° C. 45 sec, 62° C. 45 sec, 72° C. 1 min, total 25 cycles, and then 72° C. 5 min. PCR products were identified on 2% agarose-gel electrophoresis followed by image analysis software.

Figure 8:
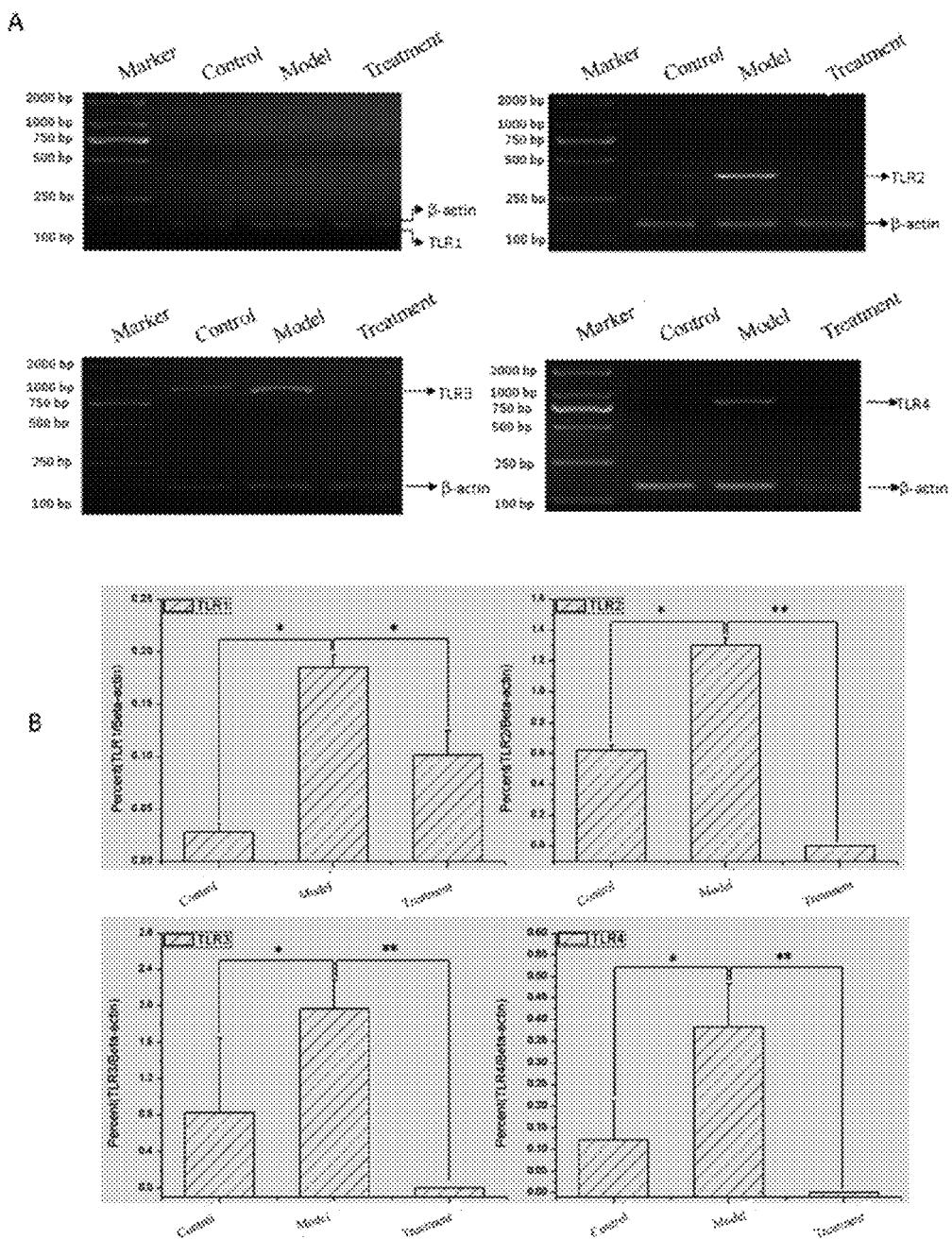
FIG. 8 The expression of TLR 1-4 gene using RT-PCR with UC after 4 h treating with 3.2 mg/kg CZLC331 protein in trinitrobenzene sulfonic acid (TNBS) modeling.
Figure 9:
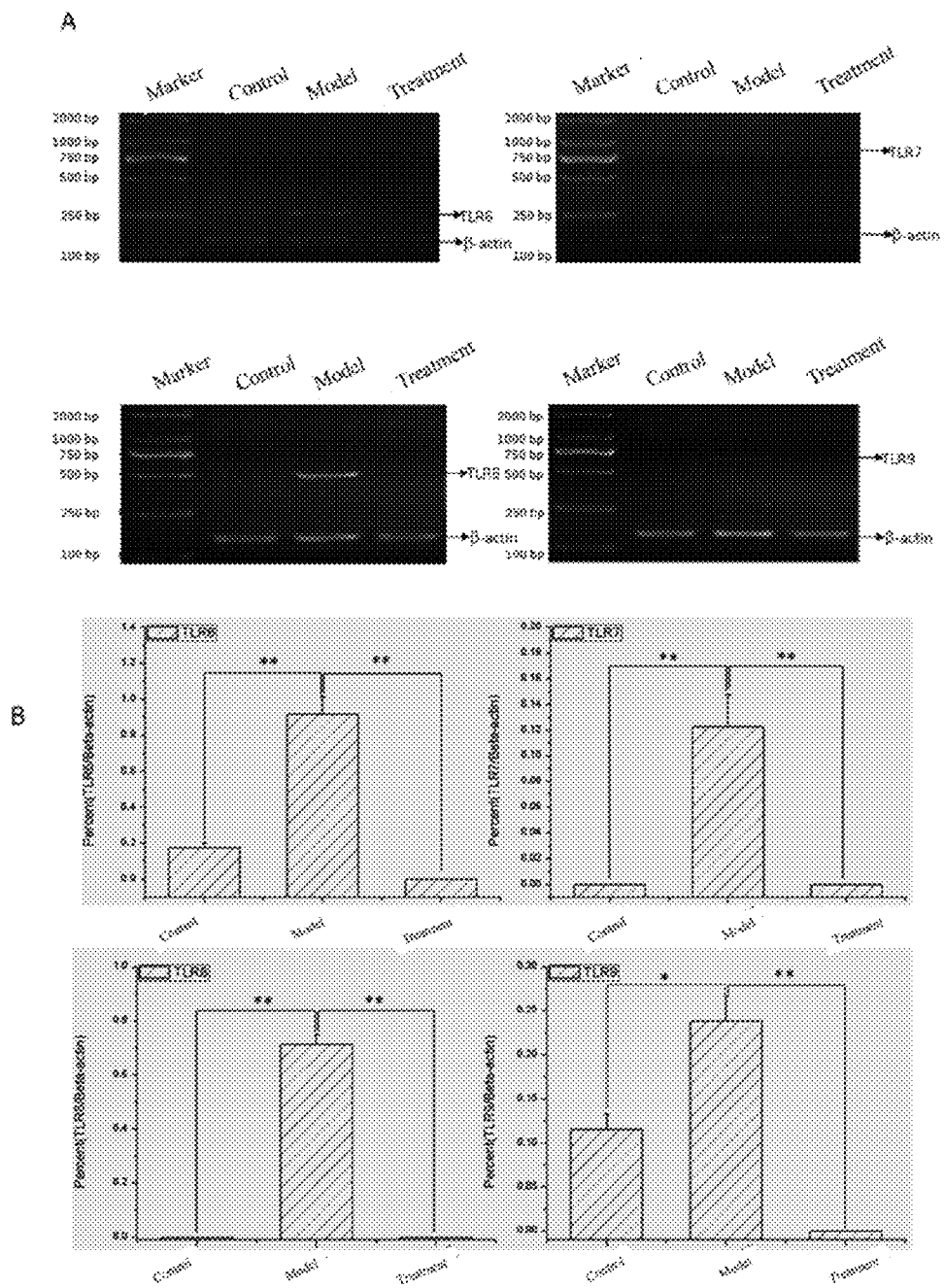
FIG. 9 The expression of TLR 6-9 gene using RT-PCR with UC after 4 h treating with 3.2 mg/kg CZLC331 protein in trinitrobenzene sulfonic acid (TNBS) modeling.

The results were that the expression of TLR family has significant differences with the model group after CZLC331 treatment in FIG. 8 and FIG. 9. The expression of TLR2, TLR3, TLR4, TLR8 and TLR9 were significantly raised,in model group, and the expression would change after CZLC331 therapy. The expression of TLR6 and TLR7 were significantly raised, in model group too, but there were no significant differences after CZLC331 therapy.

The treatment and mechanism may also be related to reduce expression of TLR family. And it suggested that the therapy of CZLC331 for IBD was effective through the pathway of TLR family, it can be become the drug for treating IBD.

TABLE 1

RT-PCR amplification with a primer sequence information

| Primer | Primer sequence |
|--------|-----------------|
| TLR1 | pU: 5'-TTGTGCCACCCAACAGTCAGCC-3' (SEQ ID NO: 7) |
|  | pD: 5'-ACCGCTCAACCCCAGGAACTGT-3' (SEQ ID NO: 8) |
| TLR2 | pU: 5'-TTCCCTGCTCGTTCTCCCAGCA-3' (SEQ ID NO: 9) |
|  | pD: 5'-TAGAGCTCTTGCAGCCGAGGCA-3' (SEQ ID NO: 10) |
| TLR3 | pU: 5'-AGCGTCTGTCCCCTCGCTCTTT-3' (SEQ ID NO: 11) |
|  | pD: 5'-GGCGGCCCGAAAACATCCTTCT-3' (SEQ ID NO: 12) |
| TLR4 | pU: 5'-GCTTCCACAAGAGCCGGAAGGT-3' (SEQ ID NO: 13) |
|  | pD: 5'-TGGCCAGGCTATCTGTGAGCGT-3' (SEQ ID NO: 14) |
| TLR6 | pU: 5'-TTCATCCACATGGTGTGCCCGC-3' (SEQ ID NO: 15) |
|  | pD: 5'-ATATGCTCTCAGCCCAGGCGCA-3' (SEQ ID NO: 16) |
| TLR7 | pU: 5'-TCAGCATGTGCCCCCAACATGG-3' (SEQ ID NO: 17) |

TABLE 1-continued

RT-PCR amplification with a primer
sequence information

| Primer | | Primer sequence |
|---|---|---|
| | pD: | 5'-CAACGGCCAGAGTTCACTGCCA-3' (SEQ ID NO: 18) |
| TLR8 | pU: | 5'-TGGCTGCTCTGGTTCACCACCT-3' (SEQ ID NO: 19) |
| | pD: | 5'-TGTTGGGCCACTGGAGGATGGA-3' (SEQ ID NO: 20) |
| TLR9 | pU: | 5'-GCCTGGTGGACTGCAATTGGCT-3' (SEQ ID NO: 21) |
| | pD: | 5'-TCACAGCGACGGCAATTCCCAC-3' (SEQ ID NO: 22) |
| β-actin | pU: | 5'-GCGAGCACAGCTTCTTTGCAGC-3' (SEQ ID NO: 23) |
| | pD: | 5'-AATACAGCCCGGGGAGCATCGT-3' (SEQ ID NO: 24) |

Example 3

The Preventive Effect of CZLC331 Protein for IBD

Experimental Animals: the same as in Example 2.
Reagents: the same as in Example 2.
Model preparation: the same as in Example 2.
Experimental animal groups: model group, prevention group and control group (n=8). The prevention group: BALB/c mice were treated therapeutically with CBLB502 (3.2 mg/kg) before TNBS administration, and then the mice were given TNBS and normal feeding two days. The model group was normal feeding two days after TNBS administration. The control mice received 38% ethanol alone by using the same method described above, and normal feeding.

Figure 10:
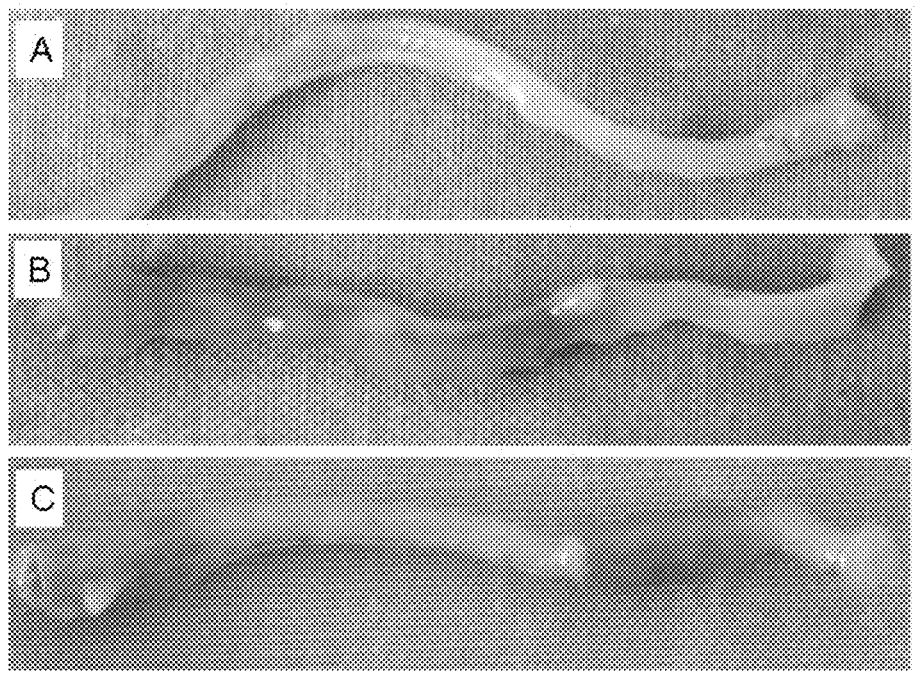
FIG. 10 The colon appearance of mice with UC before modeling 0.5 h with 0.2 mg/kg CZLC331 protein in trinitrobenzene sulfonic acid (TNBS) modeling.
Figure 11:
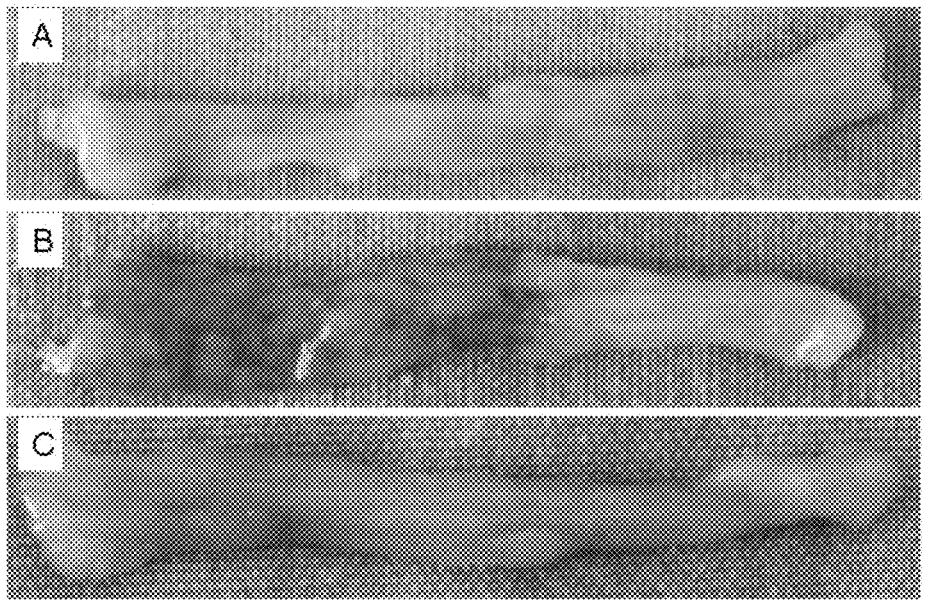
FIG. 11 The colonic mucosa of mice with UC before modeling 0.5 h with 0.2 mg/kg CZLC331 protein in trinitrobenzene sulfonic acid (TNBS) modeling.

Test contents and test methods: the same as in Example 2.
The results shown that feeding/water and activity were significantly reduced, and there were blood in the stool in model mice. There were significant congestion, edema, hemorrhage, and ulceration in modeling (FIG. 10, A. control group, B. modeling group, C. prevention group). The blood in the stool, eat less and move less were reduced, and the congestion, edema, hemorrhage began reduce (FIG. 11, A. control group, B. modeling group, C. prevention group). These results showed that CZLC331 has protective effects for the prevention of IBD, and it can be become the drug for preventing IBD.

Example 4

The Preparation of CZLC331 Injection 1.
Composition: the CZLC331 injection (5% by weight/volume (mg/mL) CZLC331 protein), 0.85% sodium chloride and water for injection.

2. The preparation method of CZLC331 protein injection:
1) The prokaryotic expression vector pET28b-Tat-CZLC331 what was constructed correctly was transformed into E. coli BL21 (DE3), and then coating to the LB plate what contain the Kana+100 μg/ml. Then the clone was inoculated into 5 ml LB containing Kana+100 μg/ml, the bacteria was shake at 220 rpm for 16 h.
2) The bacteria was recovered, and it was diluted to $OD_{600}$=0.8. Then the bacteria (5 ml) were inoculated into 150 ml LB containing Kana+ (final concentration is 100 μg/ml). The bacteria were shaking at 37° C. approximately 4-5 hours at 220 rpm. The inducing agent IPTG (final concentration 1 mM) was added rapidly to the bacteria when the $OD_{600}$ is 0.6-1.0, and it was induced and expressed at 30° C., 220rpm by 8 hours.
3) The induced and expressed bacteria were collected at 12000 rpm for 10 minutes at 4° C. The bacteria were broke by ultrasound using 20 mM sodium phosphate buffer, and was prepared a CZLC331 protein. The unpurified CZLC331 was directly loaded onto the HisTrap HP 5 ml column (purchased from GE Corporation), and then the peak baseline was washed using 4-5 column volumes of the above buffer. Finally, the protein was washed using elution buffer (20 mM Na3PO4+0.5M NaCl+0.5M imidazole, pH7.4), and then CZLC331 was obtained.
4) The CZLC331 protein was dissolved in injection water, and then sodium chloride was added, and uniformly stirred. The activated carbon what was treated by dry heat at 0.3% (weight/volume) was added to the solution for adsorbing 15 min, the solution was filtered to clarity and safekeeping. The filter includes three filters: a titanium filter for decarburizations, a 0.45 μm cartridge filter filtering and a 0.22 μm drum filter cleaning strainer.

Example 5

The Preparation of CZLC331 Protein Enteric-Coated Tablets

1. The CZLC331 protein 100 g is weight, and it is through the 100-mesh sieve. The lactose is 60 g, microcrystalline cellulose is 20 g, carboxymethyl starch sodium is 20 g, povidone $K_{30}$ 10 g through a 80-mesh sieve. The main drugs and accessories were mixed in accordance to the principle of equal increments, and then other materials is added for a 30% volume ratio. Finally, the drug is granulated through the 20 mesh and gets the wet granules.
2. The CZLC331 protein was dried for 3 hours at 55-65° C., and got dry pellets after 20-mesh sieve. The 50 g talcs were added to 2500 g pellets of CZLC331, and was mixed. The content of mixed protein was determinated. The determinated pellets were sending to a tablet machine for fitting speed and compress, and were suppressed into platode CZLC331 protein tablet what is a diameter of 1.2 cm.
3. The enteric coating was painting on platode CZLC331 tablet for about 1.0 mm. The coating material is EOBS68, the enteric coating is airtight and moisture, it has strongly coat strength and resistance to the gastric juice. The effective and safe release of drug is done through changing the pH of solution.

Efficacy Analysis:
The CZLC331 protein as the active ingredient was prepared to the drug for preventing and curing IBD. It has the following characteristics:
1) High efficiency: the experimental data show that all animals less fooding and activity, and blood in the stool have improved significantly in the treatment group and the prevention group in example 2 and example 3. These results indicated that the effective rate is 100%. The effective rate of recovered colon mucosa is 75% in treatment group. The clinical drugs sulfasalazine has the effective rate of only about 90%, and the markedly effective rate was only 50%.
2) Rapid onset: the experimental data show that all animals have effective after treating at 24 h, while the sulfasalazine take is about two weeks in example 2 and example 3.
3) The course of treatment is short (usually 5-10 days): The sulfasalazine treatment is generally about 6 weeks. The course of treatment using this drug is 1-2 days, the effect of sulfasalazine is a week or so, and the clinical onset is six weeks. Therefore, the course of treatment is 5-10 days in this invention.

4) High safe (non-toxic): The alanine aminotransferase (ALT) and aspartate aminotransferase (AST) of patients who take sulfasalazine increased, it suggested that there is liver toxicity. The CZLC331 belongs to the protein drugs, it has been used as anti-radiation drug, and it has non-toxic to the body.

5) Side effects (no significant side effects): There have nausea, rash, neutropenia after taking the sulfasalazine, this is a protein drug, it has been used as anti-radiation drug, and it has no significant side effects to the body.

6) Convenient (only once daily intraperitoneal injection): The usage of sulfasalazine is 3-4 g/d orally, and needed divided into 3-4 times a day.

Industrial Applicability

The invention provides a flagellin derivative of *Salmonella* CZLC331 in the prevention and treatment for IBD. It has high efficacy, fast onset, short course, non-toxic, small side effects, and medication convenient. The CZLC331 can solve the poor efficacy, slow onset, long course of treatment, side effects of existing treatment drugs for IBD, and it can significantly reduce the pain of patient, promote physical rehabilitation, and improve the patient's quality of life. It will be play an important role in the prevention and treatment of IBD in this invention, and it has broad application prospects.

The invention claimed is:

1. A method for the treatment of an inflammatory bowel disease (IBD) in a subject in need thereof, the method comprising administering a composition comprising a CZLC331 protein to said subject, wherein said IBD is treated, and wherein the CZLC331 protein is encoded by the nucleotide sequence of SEQ ID NO: 2.

2. A method for preventing an inflammatory bowel disease (IBD) in a subject in need thereof, the method comprising administering a composition comprising a CZLC331 protein to said subject, wherein said IBD is prevented, and wherein the CZLC331 protein is encoded by the nucleotide sequence of SEQ ID NO: 2.

3. The method of claim 1, wherein the IBD is selected from the group consisting of ulcerative colitis (UC) and Crohn's disease (CD).

4. The method of claim 1, wherein the composition comprising the CZLC331 protein is administered as an injection, an oral preparation, an enema liquid, a capsule, an enteric-coated tablet, a powder, or granules.

5. The method of claim 4, wherein the composition is administered as a capsule, an enteric-coated tablet, a powder, or granules, and wherein the CZLC331 protein is provided in an amount of 1-35 wt %.

6. The method of claim 4, wherein the composition is administered as an injection, an oral liquid, or an enema liquid, and wherein the CZLC331 protein is provided in a concentration of 2-64 g/L.

7. The method of claim 4, wherein the composition further comprises one or more pharmaceutically acceptable auxiliary materials selected from the group comprising: absorption accelerators, surfactants, lubricants, stabilizers, diluents, bonding agents, wetting agents, disintegrants, adsorption carriers, excipients, sweeteners, flavoring agents, and pigments.

8. The method of claim 4, wherein the composition is administered as an injection comprising 5% CZLC331 protein (5g/100ml), 0.85% sodium chloride (0.85g/100m1), and injectable water.

9. The method of claim 4, wherein the composition is administered as an enteric-coated tablet prepared by:
mixing and granulating 100 parts by weight of the CZLC331 protein, 60 parts by weight of lactose, 20 parts by weight of microcrystalline cellulose, 20 parts by weight of sodium carboxymethyl starch, and 10 parts by weight of Povidone K30, and
mixing the resultant granules with talc powder in a weight ratio 2500:50, tabletting to produce tablets, and spraying and coating to form an enteric coating layer on the surface of the tablets.

10. The method of claim 2, wherein the IBD is selected from the group consisting of ulcerative colitis (UC) and Crohn's disease (CD).

11. The method of claim 2, wherein the composition comprising the CZLC331 protein is administered as an injection, an oral preparation, an enema liquid, a capsule, enteric-an coated tablet, a powder, or granules.

12. The method of claim 11, wherein the composition is administered as a capsule, an enteric-coated tablet, a powder, or granules, and wherein the CZLC331 protein is provided in an amount of 1-35 wt%.

13. The method of claim 11, wherein the composition is administered as an injection, an oral liquid, or an enema liquid, and wherein the CZLC331 protein is provided in a concentration of 2-64 g/L.

14. The method of claim 11, wherein the composition further comprises one or more pharmaceutically acceptable auxiliary materials selected from the group comprising of: absorption accelerators, surfactants, lubricants, stabilizers, diluents, bonding agents, wetting agents, disintegrants, adsorption carriers, excipients, sweeteners, flavoring agents, and pigments.

15. The method of claim 11, wherein the composition is given as an injection comprising 5% CZLC331 protein (5g/100ml), 0.85% sodium chloride (0.85g/100m1), and injectable water.

16. The method of claim 11, wherein the composition is administered as a enteric-coated tablet prepared by:
mixing and granulating 100 parts by weight of CZLC331, 60 parts by weight of lactose, 20 parts by weight of microcrystalline cellulose, 20 parts by weight of sodium carboxymethyl starch, and 10 parts by weight of Povidone K30, and
mixing the resultant granules with talc powder in a weight ratio 2500:50, and tabletting to produce tablets, and spraying and coating to form an enteric coating layer on the surface of the tablets.

* * * * *

```
                         SEQUENCE LISTING

<160> NUMBER OF SEQ ID NOS: 24

<210> SEQ ID NO 1
<211> LENGTH: 891
<212> TYPE: DNA
<213> ORGANISM: Artificial Sequence
<220> FEATURE:
<223> OTHER INFORMATION: Synthetic Oligonucleotide

<400> SEQUENCE: 1
atggctcaag ttatcaacac taactctttg tctttgttga ctcaaaacaa cttgaacaag      60
tctcaatctt ctttgtcttc tgctatcgaa agattgtctt ctggtttgag aatcaactct     120
gctaaggacg acgctgctgg tcaagctatc gctaacagat tcacttctaa catcaagggt     180
ttgactcaag cttctagaaa cgctaacgac ggtatctcta tcgctcaaac tactgaaggt     240
gctttgaacg aaatcaacaa caacttgcaa agagttagag aattgtctgt tcaagctact     300
aacggtacta actctgactc tgacttgaag tctatccaag acgaaatcca acaaagattg     360
gaagaaatcg acagagtttc taaccaaact caattcaacg tgttaaggt tttgtctcaa      420 gacaaccaaa tgaagatcca agttggtgct aacgacggtg aaactatcac tatcgacttg     480
caaaagatcg acgttaagtc tttgggtttg acggtttca acgttaactc tccaggtatc      540
tctggtggtg gtggtggtat cttggactct atgggtacat tgatcaacga agacgctgct     600
gctgctaaga agtctactgc taacccattg gcttctatcg actctgcttt gtctaaggtt     660
gacgctgtta gatcttcttt gggtgctatc caaaacagat tcgactctgc tatcactaac     720
ttgggtaaca ctgttactaa cttgaactct gctagatcta gaatcgaaga cgctgactac     780
gctactgaag tttctaacat gtctaaggct caaatcttgc aacaagctgg tacttctgtt     840
ttggctcaag ctaaccaagt tccacaaaac gttttgtctt tgttgagatg a              891

<210> SEQ ID NO 2
<211> LENGTH: 996
<212> TYPE: DNA
<213> ORGANISM: Artificial Sequence
<220> FEATURE:
<223> OTHER INFORMATION: Synthetic Oligonucleotide

<400> SEQUENCE: 2
atgggcagga agaagcggag acagcgacga agaggccata tggctagcat gactggtgga      60
cagcaaatgg gtcgcggatc catggctcaa gttatcaaca ctaactcttt gtctttgttg     120
actcaaaaca acttgaacaa gtctcaatct tctttgtctt ctgctatcga agattgtct      180 tctggtttga gaatcaactc tgctaaggac gacgctgctg gtcaagctat cgctaacaga     240
ttcacttcta acatcaaggg tttgactcaa gcttctagaa acgctaacga cggtatctct     300
```

```
atcgctcaaa ctactgaagg tgctttgaac gaaatcaaca acaacttgca aagagttaga    360
gaattgtctg ttcaagctac taacggtact aactctgact ctgacttgaa gtctatccaa    420
gacgaaatcc aacaaagatt ggaagaaatc gacagagttt ctaaccaaac tcaattcaac    480
ggtgttaagg ttttgtctca agacaaccaa atgaagatcc aagttggtgc taacgacggt    540
gaaactatca ctatcgactt gcaaaagatc gacgttaagt ctttgggttt ggacggtttc    600
aacgttaact ctccaggtat ctctggtggt ggtggtggta tcttggactc tatgggtaca    660
ttgatcaacg aagacgctgc tgctgctaag aagtctactg ctaacccatt ggcttctatc    720
gactctgctt tgtctaaggt tgacgctgtt agatcttctt gggtgctat ccaaaacaga     780 ttcgactctg ctatcactaa cttgggtaac actgttacta acttgaactc tgctagatct    840
agaatcgaag acgctgacta cgctactgaa gtttctaaca tgtctaaggc tcaaatcttg    900
caacaagctg gtacttctgt tttggctcaa gctaaccaag ttccacaaaa cgttttgtct    960
ttgttgagac tcgagcacca ccaccaccac cactga                              996
```

<210> SEQ ID NO 3
<211> LENGTH: 331
<212> TYPE: PRT
<213> ORGANISM: Artificial Sequence
<220> FEATURE:
<223> OTHER INFORMATION: synthetic polypeptide

<400> SEQUENCE: 3

```
Met Gly Arg Lys Lys Arg Arg Gln Arg Arg Gly His Met Ala Ser
1               5                   10                  15

Met Thr Gly Gly Gln Gln Met Gly Arg Gly Ser Met Ala Gln Val Ile
                20                  25                  30

Asn Thr Asn Ser Leu Ser Leu Leu Thr Gln Asn Asn Leu Asn Lys Ser
                35                  40                  45

Gln Ser Ser Leu Ser Ser Ala Ile Glu Arg Leu Ser Ser Gly Leu Arg
            50                  55                  60

Ile Asn Ser Ala Lys Asp Asp Ala Ala Gly Gln Ala Ile Ala Asn Arg
65                  70                  75                  80

Phe Thr Ser Asn Ile Lys Gly Leu Thr Gln Ala Ser Arg Asn Ala Asn
                    85                  90                  95

Asp Gly Ile Ser Ile Ala Gln Thr Thr Glu Gly Ala Leu Asn Glu Ile
                100                 105                 110

Asn Asn Asn Leu Gln Arg Val Arg Glu Leu Ser Val Gln Ala Thr Asn
            115                 120                 125

Gly Thr Asn Ser Asp Ser Asp Leu Lys Ser Ile Gln Asp Glu Ile Gln
        130                 135                 140

Gln Arg Leu Glu Glu Ile Asp Arg Val Ser Asn Gln Thr Gln Phe Asn
145                 150                 155                 160

Gly Val Lys Val Leu Ser Gln Asp Asn Gln Met Lys Ile Gln Val Gly
                165                 170                 175

Ala Asn Asp Gly Glu Thr Ile Thr Ile Asp Leu Gln Lys Ile Asp Val
                180                 185                 190

Lys Ser Leu Gly Leu Asp Gly Phe Asn Val Ser Pro Gly Ile Ser
            195                 200                 205

Gly Gly Gly Gly Gly Ile Leu Asp Ser Met Gly Thr Leu Ile Asn Glu
        210                 215                 220

Asp Ala Ala Ala Ala Lys Lys Ser Thr Ala Asn Pro Leu Ala Ser Ile
225                 230                 235                 240
```

```
Asp Ser Ala Leu Ser Lys Val Asp Ala Val Arg Ser Leu Gly Ala
            245                 250                 255

Ile Gln Asn Arg Phe Asp Ser Ala Ile Thr Asn Leu Gly Asn Thr Val
        260                 265                 270

Thr Asn Leu Asn Ser Ala Arg Ser Arg Ile Glu Asp Ala Asp Tyr Ala
        275                 280                 285

Thr Glu Val Ser Asn Met Ser Lys Ala Gln Ile Leu Gln Gln Ala Gly
        290                 295                 300

Thr Ser Val Leu Ala Gln Ala Asn Gln Val Pro Gln Asn Val Leu Ser
305                 310                 315                 320

Leu Leu Arg Leu Glu His His His His His His
            325                 330
```

<210> SEQ ID NO 4
<211> LENGTH: 296
<212> TYPE: PRT
<213> ORGANISM: Artificial Sequence
<220> FEATURE:
<223> OTHER INFORMATION: synthetic polypeptide

<400> SEQUENCE: 4

```
Met Ala Gln Val Ile Asn Thr Asn Ser Leu Ser Leu Thr Gln Asn
1               5                   10                  15

Asn Leu Asn Lys Ser Gln Ser Ser Leu Ser Ser Ala Ile Glu Arg Leu
            20                  25                  30

Ser Ser Gly Leu Arg Ile Asn Ser Ala Lys Asp Asp Ala Ala Gly Gln
        35                  40                  45

Ala Ile Ala Asn Arg Phe Thr Ser Asn Ile Lys Gly Leu Thr Gln Ala
    50                  55                  60

Ser Arg Asn Ala Asn Asp Gly Ile Ser Ile Ala Gln Thr Thr Glu Gly
65                  70                  75                  80

Ala Leu Asn Glu Ile Asn Asn Asn Leu Gln Arg Val Arg Glu Leu Ser
                85                  90                  95

Val Gln Ala Thr Asn Gly Thr Asn Ser Asp Ser Asp Leu Lys Ser Ile
            100                 105                 110

Gln Asp Glu Ile Gln Gln Arg Leu Glu Glu Ile Asp Arg Val Ser Asn
        115                 120                 125

Gln Thr Gln Phe Asn Gly Val Lys Val Leu Ser Gln Asp Asn Gln Met
    130                 135                 140

Lys Ile Gln Val Gly Ala Asn Asp Gly Glu Thr Ile Thr Ile Asp Leu
145                 150                 155                 160

Gln Lys Ile Asp Val Lys Ser Leu Gly Leu Asp Gly Phe Asn Val Asn
                165                 170                 175

Ser Pro Gly Ile Ser Gly Gly Gly Gly Ile Leu Asp Ser Met Gly
            180                 185                 190

Thr Leu Ile Asn Glu Asp Ala Ala Ala Lys Lys Ser Thr Ala Asn
        195                 200                 205

Pro Leu Ala Ser Ile Asp Ser Ala Leu Ser Lys Val Asp Ala Val Arg
    210                 215                 220

Ser Ser Leu Gly Ala Ile Gln Asn Arg Phe Asp Ser Ala Ile Thr Asn
225                 230                 235                 240

Leu Gly Asn Thr Val Thr Asn Leu Asn Ser Ala Arg Ser Arg Ile Glu
                245                 250                 255

Asp Ala Asp Tyr Ala Thr Glu Val Ser Asn Met Ser Lys Ala Gln Ile
            260                 265                 270
```

```
Leu Gln Gln Ala Gly Thr Ser Val Leu Ala Gln Ala Asn Gln Val Pro
        275                 280                 285

Gln Asn Val Leu Ser Leu Leu Arg
    290                 295
```

```
<210> SEQ ID NO 5
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 5
cgcgggatcc atggctcaag ttatca                                          26

<210> SEQ ID NO 6
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 6
ccgctcgagt ctcaacaaag acaagtt                                         27

<210> SEQ ID NO 7
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 7
ttgtgccacc caacagtcag cc                                              22

<210> SEQ ID NO 8
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 8
accgctcaac cccaggaact gt                                              22

<210> SEQ ID NO 9
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 9
ttccctgctc gttctcccag ca                                              22

<210> SEQ ID NO 10
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 10
tagagctctt gcagccgagg ca                                              22
```

```
<210> SEQ ID NO 11
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 11
agcgtctgtc ccctcgctct tt                                            22

<210> SEQ ID NO 12
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 12
ggcggcccga aaacatcctt ct                                            22

<210> SEQ ID NO 13
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 13
gcttccacaa gagccggaag gt                                            22

<210> SEQ ID NO 14
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 14
tggccaggct atctgtgagc gt                                            22

<210> SEQ ID NO 15
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 15
ttcatccaca tggtgtgccc gc                                            22

<210> SEQ ID NO 16
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 16
atatgctctc agcccaggcg ca                                            22

<210> SEQ ID NO 17
<211> LENGTH: 22
<212> TYPE: DNA
<213> ORGANISM: Artificial Sequence
<220> FEATURE:
<223> OTHER INFORMATION: synthetic oligonucleotide
```

```
<400> SEQUENCE: 17
tcagcatgtg cccccaacat gg                                              22

<210> SEQ ID NO 18
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 18
caacggccag agttcactgc ca                                              22

<210> SEQ ID NO 19
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 19
tggctgctct ggttcaccac ct                                              22

<210> SEQ ID NO 20
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 20
tgttgggcca ctggaggatg ga                                              22

<210> SEQ ID NO 21
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 21
gcctggtgga ctgcaattgg ct                                              22

<210> SEQ ID NO 22
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 22
tcacagcgac ggcaattccc ac                                              22

<210> SEQ ID NO 23
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 23
gcgagcacag cttctttgca gc                                              22

<210> SEQ ID NO 24
```

```
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 24
aatacagccc ggggagcatc gt                                              22
```